United States Patent [19]

Turney

[11] 4,280,994
[45] Jul. 28, 1981

[54] ANTIPERSPIRANT STICK COMPOSITIONS

[75] Inventor: Mary E. Turney, Briarcliff Manor, N.Y.

[73] Assignee: Union Carbide Corporation, New York, N.Y.

[21] Appl. No.: 767,489

[22] Filed: Feb. 10, 1977

[51] Int. Cl.$^3$ .......................... A61K 7/32; A61K 7/38
[52] U.S. Cl. ................................ 424/68; 424/DIG. 5; 424/65; 424/66; 424/67; 424/184
[58] Field of Search ....................... 424/68, 65, DIG. 5

[56] References Cited

U.S. PATENT DOCUMENTS

| | | | |
|---|---|---|---|
| 2,617,754 | 11/1952 | Neely | 424/DIG. 5 |
| 3,300,387 | 11/1967 | Kole | 424/68 |
| 3,324,004 | 6/1967 | Nagler | 424/68 |

FOREIGN PATENT DOCUMENTS

| | | | |
|---|---|---|---|
| 2241030 | 3/1973 | Fed. Rep. of Germany | 424/47 |
| 2365219 | 12/1973 | Fed. Rep. of Germany | 424/68 |
| 2442314 | 3/1975 | Fed. Rep. of Germany | 424/47 |
| 844769 | 9/1961 | France | 424/66 |
| 7103689 | 9/1971 | Netherlands | 424/47 |

Primary Examiner—Dale R. Ore
Attorney, Agent, or Firm—Franklyn Schoenberg

[57] ABSTRACT

Antiperspirant stick compositions comprised of polyethylene glycol exhibit improved aesthetic properties and efficacy.

16 Claims, No Drawings

ANTIPERSPIRANT STICK COMPOSITIONS

BACKGROUND OF THE INVENTION

This invention relates to stick-form anti-perspirant compositions. More particularly, this invention relates to an improved antiperspirant stick composition characterized by superior aesthetic properties and antiperspirant efficacy.

Antiperspirant stick compositions are well known. Conventional anti-perspirant stick compositions are typically composed of a stearate soap-alcohol delivery system and an antiperspirant agent, usually aluminum chlorhydroxy lactate complex. Such antiperspirant sticks are not widely acceptable due to a number of inherent deficiencies, namely lack of efficacy and relatively poor aesthetic properties. It is generally recognized that the alkaline pH of stearate soap-alcohol based stick compositions tends to inactivate aluminum chlorhydroxide, the most effective and commonly used astringent and antiperspirant salt, consequently, there is a considerable reduction in the efficacy when aluminum chlorohydroxide is used in these compositions. In addition, soap-alcohol based stick compositions exhibit considerable drag on the skin during application and also leave a moist, tacky residue on the skin after application.

Because of the relatively low efficacy of traditional soap-alcohol based stick compositions, the toiletries industry has vigorously explored more effective alternative delivery systems. One typical system is composed of a wax-like matrix which serves as a carrier for aluminum chlorhydroxide and a volatile silicone composition. In the majority of the stick compositions presently on the market, stearyl alcohol is used as the support matrix and assorted cyclic dimethyl siloxane compounds are used as the volatile silicone component. While these more modern antiperspirant stick compositions are more effective as antiperspirants and leave a fairly dry residue on application to the skin, they also have a number of inherent deficiencies. These stick compositions tend to drag during application and are lacking in internal cohesion, dimensional stability and homogeneity. In addition, these stick compositions do not include water-soluble components to assist in activating the aluminum chlorhydroxide salts in the presence of perspiration and they exhibit a whitening effect produced by a powdery residue remaining on the skin after application. After storage at 40° C. for 24 hours they exhibit even greater distortion, lack of internal cohesion and drag on the skin.

It is, therefore, an object of this invention to provide an effective, inert, non-irritating, non-tacky and cosmetically attractive antiperspirant stick composition that also exhibits improved internal cohesion homogeneity, dimensional stability, ease of application and generally improved aesthetic properties together with a high order of astringent and antiperspirant efficacy. Another object of this invention is to provide an improved delivery system that permits the active astringent and antiperspirant salt to be delivered on to the skin without diminution in antiperspirant activity. Other objects and advantages will become readily apparent from the following description and appended claims.

SUMMARY OF THE INVENTION

We have found that the addition of polyethylene glycol having a molecular weight of from about 950 to about 1600 to conventional antiperspirant stick compositions provides a dramatically improved composition which not only exhibits excellent antiperspirant activity, but at the same time is aesthetically and cosmetically more appealing. The stick compositions of this invention are extremely stable and highly resistant to heat distortion. They exhibit improved cohesiveness and are outstanding in their ease of application. They also are substantially non-irritating and inert to the skin from a toxicological view point.

The improved antiperspirant stick compositions of this invention are comprised of:

A. From about 35 to about 55 weight percent of one or more volatile silicone compositions;

B. From about 15 to about 35 weight percent of one or more materials having wax like characteristics;

C. From about 18 to about 50 weight percent of one or more compounds having antiperspirant properties; and D. From about 2 to about 10 weight percent of a polyethylene glycol composition having an average molecular weight within the range of from about 950 to about 1600.

All weight percents are based on the total weight of the antiperspirant stick composition.

DETAILED DESCRIPTION OF THE PREFERRED EMBODIMENT

The antiperspirant stick composition of this invention includes from about 35 to about 55 weight percent of one or more low molecular weight volatile silicone compositions having a boiling point of less than 300° C. at 760 mm. of Hg. The specific volatile silicone compositions which are useful and their manner of use are well known to those skilled in the art and will not be described in great detail. Illustrative of useful volatile silicone compositions are cyclic dimethyl siloxane composition corresponding to the following structural formula:

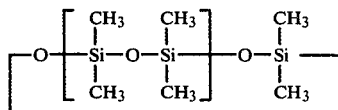

wherein: n=2, 3, 4 or 5 and mixtures thereof.

Linear volatile silicone compositions or mixtures of linear volatile silicone and cyclic volatile silicone compositions can also be employed as components of the antiperspirant stick compositions of this invention, provided that the volatility is sufficiently high so that no oily residue remains on the skin. Illustrative examples of linear silicone compositions which may be used in this manner are dimethylsiloxane compositions having a viscosity of less than 5 centistokes at 25° C.

Volatile silicone compositions useful as ingredients in the antiperspirant stick compositions of this invention are commercially available products at this time. For example, a mixture of cyclic tetramer compositions with minor amounts of the cyclic pentamer and trimer compositions is available from Union Carbide Corporation under the product disignation Union Carbide Silicone Y-7207. A particularly preferred cyclic dimethyl siloxane composition, which is essentially a mixture of from about 95 to about 98 weight percent of the cyclic pentamer composition with minor amounts of the cyclic tetramer and hexamer compositions, is available from Union Carbide Corporation under the product designation Union Carbide Silicone 7158.

The antiperspirant stick compositions of this invention include from about 15 to about 35 weight percent of one or more materials having wax-like characteristics. The waxy component functions as the basic structural matrix of the stick composition and as an emollient. In general, specific waxy materials suitable for use in stick compositions, as well as the manner of their use, are well known. Wax-like materials having a melting point from about 45° C. to about 75° C. are preferred for use in the stick compositions of this invention. Useful wax-like materials include fatty acids, fatty alcohols, fatty acid esters and fatty acid amides, each having from 8 to 30 carbon atoms. Illustrative of preferred wax-like materials are cetyl alcohol, palmitic acid, isopropyl palmitate, stearyl alcohol, lauryl alcohol, behenamide, the sucrose esters of tallow fatty acids, the mono- and di-fatty acid esters of polyethylene glycol and the like. Particularly, preferred wax-like materials are stearyl alcohol, cetyl alcohol, a sucrose ester of a tallow fatty acid available from Croda Inc. under the product designation Crodesta A10 and the distearate ester of polyethylene glycol having an average molecular weight of from about 6000 to about 7500, which is available from Armak Division, Akzona Corporation under the product designation Polyethylene Glycol 6000 Distearate.

The antiperspirant stick compositions of this invention include from about 20 to about 50 weight percent and preferably from about 20 to about 30 weight percent of one or more compounds having antiperspirant properties. Useful antiperspirant compounds and their manner of preparation and use are well known. In general, the most useful antiperspirant compounds are the inorganic and organic salts of aluminum, zirconium and zinc or mixtures thereof. Useful antiperspirant salt includes sulfate, bromide, chloride, chlorhydroxide, lactate, sulfonate or like salts. Illustrative of useful antiperspirant compositions are aluminum chlorhydroxide, aluminum sulfate, a mixture of aluminum chlorhydroxide and zirconium chlorhydroxide, aluminum phenolsulfonate, aluminum chloride, aluminum bromide and zinc phenolsulfonate, aluminum chlorhydroxide being particularly preferred. Preferred antiperspirant compounds also exhibit astringent properties. It is essential that the antiperspirant composition be in the form of a powder and of a particle sufficiently small to insure complete and uniform dispersion throughout the stick composition during formulation.

An essential component of the antiperspirant stick compositions of this invention is a polyethylene glycol composition corresponding to the following general formula:

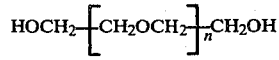

where n represents a whole number of sufficient magnitude to provide a polyethylene glycol composition having an average molecular weight of from about 950 to about 1600.

Preferred, polyethylene glycol compositions are those having a formula molecular weight within the range of from about 1300 to about 1600 and those having an average molecular weight within the range of from about 950 to about 1050. Alternatively polyethylene glycol blends containing up to 75 weight percent polyethylene glycol composition having an average molecular weight within the range of from about 1300 to about 1600 and the remainder being polyethylene glycol composition having an average molecular weight within the range of from about 950 to about 1050, all weight percents being based on the total weight of the blend are also preferred.

Polyethylene glycol compositions having an average molecular weight within the stated ranges are commercially available products. Suitable compositions can also be prepared by well known synthetic procedures. Polyethylene glycol having an average molecular weight range of from about 1300 to about 1600 and polyethylene glycol having an average molecular weight of from about 950 to about 1050 are both available from Union Carbide Corporation under the product designation CARBOWAX Polyethylene Glycol 1540 and CARBOWAX Polyethylene Glycol 1000, respectively.

The quantity of polyethylene glycol employed in the antiperspirant stick compositions of this invention may range from about 2 to about 10 and is preferably from 2 to about 5 weight percent, all weight percents being based on the total weight of the stick compositions. The weight percent and the average molecular weight of the polyethylene glycol component are the critical and decisive factors which are essential to achieve the overall improved aesthetic properties of the antiperspirant stick compositions of this invention. Compositions having greater than 10 weight percent of polyethylene glycol either separate into two distinct layers on formulation or exhibit excessive graininess, flakiness, lack of internal cohesion and overall inferior aesthetic properties. Antiperspirant stick compositions in which the polyethylene glycol component has an average molecular weight either less than 950 or greater than 1600 are also aesthetically and cosmetically unacceptable.

Optional materials may be added to the basic composition for various specific purposes. Such other ingredients include but are not limited to medicaments, perfumes, oils, coloring agents, pigments, fillers, stabilizing agents, germicides and the like.

The antiperspirant stick compositions of this invention can be conveniently prepared by a simple blending of the ingredients in the above indicated weight percents. However, it is preferred to prepare the composition by first heating volatile silicone component to approximately 65° C., after which the polyethylene glycol component is added with gentle stirring. After the polyethylene glycol is melted and thoroughly mixed with the volatile silicone, the waxy materials are added to the melt, with stirring, followed by addition of aluminum chlorhydroxide which is uniformly mixed and dispersed throughout the melt. The optional ingredients may then be added. The melt may then be allowed to cool to the solidification point.

The following examples are provided to more clearly illustrate this invention. In EXAMPLES I and II:

CHLORHYDROL: is an impalpable grade of aluminum chlorhydroxide available from Reheis Chemical Company, a division of Armour Pharmaceutical Company, under the product designation Chlorhydrol.

CARBOWAX 1000: is polyethylene glycol having an average molecular weight of from about 950 to about 1050 which is available from Union Carbide Corporation under the product designation CARBOWAX Polyethylene Glycol 1000.

CARBOWAX 1540: is polyethylene glycol having an average molecular weight of from about 1300 to about 1600 which is available from Union Carbide Corporation under the product designation CARBOWAX Polyethylene Glycol 1540.

CRODESTO A10: is the sucrose ester of tallow fatty acids mp 43°-49° C. which is available from Croda, Inc. under the product designation Crodesta A10.

VOLATILE SILICONE 7158: is a cyclic dimethyl siloxane composition which is essentially a mixture of from about 95 to about 98 weight percent of the cyclic pentamer composition with minor amounts of the cyclic hexamer and tetramer compositions, available from Union Carbide Corporation under the product designation Union Carbide Silicone 7158.

POLYETHYLENE GLYCOL 400 MONOLAURATE: is the monolaurate ester of polyethylene glycol having an average molecular weight of from about 380 to about 420.

POLYETHYLENE GLYCOL 6000 DISTEARATE: is the distearate ester of polyethylene glycol having an average molecular weight of from about 6000 to about 7500.

EXAMPLE I

In Table I below are set forth a number of representative antiperspirant stick compositions of this invention which illustrate the wide range of compositions possible in the practice of this invention. The compositions of Table I were prepared as follows:

One or more waxy materials and polyethylene glycol were combined in a suitable container, heated to 80° C. and gently stirred until the wax-like materials and the polyethylene glycol were melted and well intermixed. Next aluminum chlorhydroxide was stirred into the melt and thoroughly dispersed therein. The mixture was allowed to cool to about 70° C. at which time the volatile silicone component was added and mixed in rapidly over a time period of from about 30 to about 51 seconds at which point the melt was poured into a mold and allowed to solidify over a 24 hour period.

The components and weight percent compositions of these representative compositions are as set forth in Table I below.

chlorhydroxide powder and a volatile silicone. Stearyl alcohol was used as the wax-like matrix and volatile Silicone 7158 was used as the volatile silicone component.

The composition of EXAMPLE II was prepared by the method described in EXAMPLE I.

EXAMPLE II

| Ingredient | Percent by Weight |
| --- | --- |
| Volatile Silicone 7158 | 55 |
| Chlorhydrol | 25 |
| Stearyl Alcohol | 20 |

The aesthetic properties of the conventional antiperspirant stick composition of EXAMPLE II were compared with those of EXAMPLES I(3) and I(5). The procedure is as follows: After each stick composition had set for at least 24 hours, it was examined to determine its aesthetic properties. First, the general appearance and homogeniety of the upper end of the stick were assessed. The end of the stick composition was initially evaluated to determine if it had a smooth, homogeneous appearance with little or no evidence or graininess or discrete particles. The stick was also examined for evidence of shrinkage or cavitation. The stick was then pushed from the cartridge and again examined as to the general appearance and homogeneity of the sides of the stick. An examination was then made for evidence of any tendency of the stick to crumble on simply touching or upon application to the skin. The stick composition was then stored at 42° C. for 24 hours and examined for evidence of heat distortion. Other aesthetic characteristics of the stick, such as ease of application, after-feel, greasiness, whitening effect, smoothness were evaluated by application of the stick to the back of the hand of a human subject. After the initial evaluation the stick composition was then evaluated by approximately ten human subjects under actual use conditions.

The results of this evaluation are set forth in TABLE II below. The system uses a grading scale of A, B and C, with a grading of A representing excellent, a grading of B representing fair and a grading of C representing non-acceptable.

TABLE I

ANTIPERSPIRANT STICK COMPOSITIONS
FORMULATIONS AND AMOUNTS BY WEIGHT

| Components | 1 | 2 | 3 | 4 | 5 | 6 | 7 | 8 | 9 | 10 | 11 | 12 | 13 | 14 | 15 | 16 |
| --- | --- | --- | --- | --- | --- | --- | --- | --- | --- | --- | --- | --- | --- | --- | --- | --- |
| VOLATILE SILICONE 7158 | 46 | 46 | 46 | 46 | 46 | 46 | 46 | 46 | 46 | 46 | 46 | 46 | 46 | 46 | 46 | 46 |
| CHLORHYDROL | 20 | 20 | 20 | 20 | 20 | 20 | 20 | 20 | 20 | 20 | 20 | 20 | 20 | 20 | 20 | 20 |
| CARBOWAX 1540 | — | — | 2 | 2 | 4 | 8 | 2 | — | 10 | 6 | — | 2 | 4 | 2 | 2 | 2 |
| CARBOWAX 1000 | 4 | 4 | 2 | 2 | — | — | 2 | 10 | — | 4 | 4 | 2 | — | 2 | 2 | 2 |
| WAX-LIKE MATERIAL | | | | | | | | | | | | | | | | |
| A. Stearyl Alcohol | 24 | 20 | 24 | 30 | 24 | 20 | — | — | — | — | — | — | — | — | — | — |
| B. Cetyl Alcohol | — | 4 | — | — | — | — | — | — | — | — | — | — | — | 2 | 0 | — |
| C. Polyethylene Glycol 6000 Distearate | 6 | 6 | 6 | — | 6 | 6 | 30 | — | — | — | 6 | 6 | 6 | 4 | — | — |
| D. Crodesta A-10 | — | — | — | — | — | — | — | 24 | 24 | 24 | 24 | 24 | 24 | 24 | 24 | 24 |
| E. Polyethylene Glycol 400 Monolaurate | — | — | — | — | — | — | — | — | — | — | — | — | — | — | 6 | — |
| F. Glycerol Monolaurate | — | — | — | — | — | — | — | — | — | — | — | — | — | — | — | 6 |

To compare the relative aesthetic properties of known antiperspirant stick compositions and the stick compositions of this invention, a conventional formulation was prepared which consisted essentially of a wax-like matrix which served as a carrier for aluminum

TABLE II

| EXAMPLE | AESTHETIC PROPERTIES | | | | | | | |
|---|---|---|---|---|---|---|---|---|
| | WHITENING EFFECT | CAVITATION | SHRINKAGE | COHESIVENESS | HEAT DISTORTION | EASE OF APPLICATION | GRAININESS | GREASINESS |
| II | C | B | B | C | C | B | C | A |
| I(3) | B | A | A | A | A | A | B | A |
| I(5) | B | A | A | A | A | A | B | A |

The results of the subjective comparison testing illustrate the overall enhanced aesthetic properties of the antiperspirant stick compositions of this invention in comparison with the aesthetic properties of conventional stick compositions. For example, the conventional stick composition of EXAMPLE II had a grainy appearance, tended to crumble near the edges when applied to the skin, did not rub-out smoothly on the skin, exhibited considerable drag and heat distortion and exhibited a whitening effect due to a white residue left on the skin after application. These overall unacceptable aesthetic properties are to be contrasted with the overall superior aesthetic properties exhibited by the antiperspirant stick compositions of EXAMPLES I(3) and I(5), which are representative examples of the antiperspirant stick composition of the present invention. The stick composition of EXAMPLES I(3) and I(5) were effective as anti-perspirants, inert, non-irritating, non-tacky, and did not exhibit a whitening effect on the skin. In addition, the representative stick compositions of this invention exhibited improved internal cohesion, homogeneity, dimensional stability, ease of application to the skin and general overall improved aesthetic properties, all of which are critical and very important factors which are determinative of the ultimate utility of antiperspirant stick compositions.

What is claimed is:

1. An antiperspirant stick composition comprising:
   A. from about 35 to about 55 parts of one or more volatile silicone composition; having a boiling point of less than 300° C. at 760 mm. of Hg.
   B. from about 15 to about 35 parts of one or more materials having wax-like characteristics;
   C. from about 18 to about 50 parts of one or more compounds having antiperspirant properties; and
   D. from about 2 to about 10 parts of a polyethylene glycol composition having an average molecular weight within the range of from about 950 to about 1600.

2. A composition according to claim 1 wherein said polyethylene glycol composition has an average molecular weight of from about 1300 to about 1600.

3. A composition according to claim 1 wherein said polyethylene glycol composition has an average molecular weight of from about 950 to 1050.

4. A composition according to claim 1 wherein said polyethylene glycol composition is a blend containing up to 75 weight percent polyethylene glycol having an average molecular weight of from about 1300 to about 1600, the remainder being polyethylene glycol having an average molecular weight of from about 950 to about 1050 based on the total weight of the blend.

5. A composition according to claim 4 wherein said polyethylene glycol composition is a blend containing about 50 weight percent polyethylene glycol having an average molecular weight of from about 1300 to about 1600 and about 50 weight percent polyethylene glycol having an average molecular weight of from about 950 to about 1050.

6. A composition according to claim 1 containing from about 4 to about 8 parts of said polyethylene glycol composition.

7. A composition according to claim 2 containing from about 4 to about 8 parts of said polyethylene glycol composition.

8. A composition according to claim 3 containing from about 4 to about 8 parts of said polyethylene glycol composition.

9. A composition according to claim 4 containing from 4 to about 8 parts of said polyethylene glycol composition.

10. A composition according to claim 5 containing from about 4 to about 8 parts polyethylene glycol composition.

11. A composition according to claim 1 wherein said volatile silicone is selected from the group consisting of:
    (a) cyclic dimethyl siloxane composition of the formula:

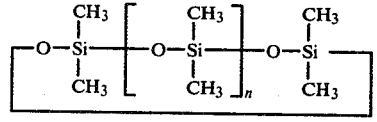

wherein n is 2, 3, 4 or 5 and mixtures thereof; and
    (b) linear dimethyl siloxane compositions having a viscosity of less than 5 centistokes at 25° C.

12. A composition according to claim 1 wherein said materials having wax-like characteristics have a melting point of from about 45° C. to about 75° C.

13. A composition according to claim 10 wherein said materials having wax-like characteristics are selected from the group consisting of cetyl alcohol, stearyl alcohol, sucrose esters of tallow fatty acids and the di-fatty acid esters of polyethylene glycol.

14. An antiperspirant stick composition comprising:
    A. 46 parts of a mixture of from about 95 to 98 weight percent decamethylcyclopentasiloxane with minor amounts of octamethylcyclotetrasiloxane and dodecamethylcyclohexasiloxane;
    B. 20 parts aluminum chlorhydroxide;
    C. 24 parts stearyl alcohol;
    D. 6 parts of the distearate ester of polyethylene glycol having an average molecular weight of from about 6000 to about 7500;
    E. 4 parts polyethylene glycol having an averge molecular weight of from about 1300 to about 1600.

15. An antiperspirant stick composition comprising:
    A. 46 parts of a mixture of from about 95 to about 98 weight percent decamethylcyclopentasiloxane with minor amounts of octamethylcyclotetrasiloxane and dodecamethylcyclohexasiloxane;
    B. 24 parts stearyl alcohol;
    C. 20 parts aluminum chlorhydroxide;
    D. 6 parts of the distearate ester of polyethylene glycol having an average molecular weight of from about 6000 to about 7500;

E. 4 parts of a polyethylene glycol blend containing about 50 weight percent polyethylene glycol having an average molecular weight of from about 1300 to about 1600 and about 50 weight percent polyethylene glycol having an average molecular weight of from about 950 to about 1050.

16. An antiperspirant stick composition comprising:
A. 46 parts of mixture of from about 95 to about 98 weight percent decamethylcyclopentasiloxane with minor amounts of octamethylcyclotetrasiloxane and dodecamethylcyclohexasiloxane;
B. 20 parts aluminum chlorhydroxide;
C. 24 parts of the sucrose ester of tallow fatty acids;
D. 6 parts of the distearate ester of polyethylene glycol having an average molecular weight of from about 6000 to about 7500;
E. 4 parts of a polyethylene glycol blend containing about 50 weight percent polyethylene glycol having an average molecular weight of from about 1300 to about 1600 and about 50 weight percent polyethylene glycol having an average molecular weight of from about 950 to about 1050.

* * * * *